United States Patent [19]

Wu

[11] Patent Number: 5,248,645
[45] Date of Patent: Sep. 28, 1993

[54] ETHYLENE OLIGOMERIZATION

[75] Inventor: An-hsiang Wu, Bartlesville, Okla.

[73] Assignee: Phillips Petroleum Company, Bartlesville, Okla.

[21] Appl. No.: 978,559

[22] Filed: Nov. 19, 1992

Related U.S. Application Data

[62] Division of Ser. No. 937,774, Sep. 1, 1992, Pat. No. 5,210,360.

[51] Int. Cl.$^5$ .............................................. B01J 31/00
[52] U.S. Cl. .................................... 502/155; 502/161; 502/162
[58] Field of Search ........................ 502/155, 162, 161

[56] References Cited

U.S. PATENT DOCUMENTS

| | | | |
|---|---|---|---|
| 4,142,060 | 2/1979 | Kuntz | 502/162 |
| 4,482,640 | 11/1984 | Knudsen et al. | 502/161 |
| 4,487,847 | 12/1984 | Knudsen | 502/155 |
| 4,859,664 | 8/1989 | Van Broekhoven et al. | 502/162 |

*Primary Examiner*—Patrick P. Garvin
*Assistant Examiner*—E. D. Irzinski
*Attorney, Agent, or Firm*—Carl D. Corvin

[57] ABSTRACT

An ethylene oligomerization catalyst system is provided that is produced by the process consisting essentially of: contacting an organonickel compound, an aromatic acid compound, and a phosphine compound. Additionally, an ethylene oligomerization process is provided that consists essentially of oligomerizing ethylene with the above-mentioned oligomerization catalyst system.

11 Claims, No Drawings

ETHYLENE OLIGOMERIZATION

CROSS REFERENCE TO RELATED APPLICATION

This application is a divisional of application Ser. No. 937,774, filed Sep. 1, 1992, and now U.S. Pat. No. 5,210,360, the entire disclosure of which is hereby incorporated by reference.

BACKGROUND OF THE INVENTION

A variety of catalysts, both homogeneous and heterogeneous, have been disclosed as oligomerization and dimerization catalysts for ethylene. For example, U.S. Pat. No. 4,482,640 and U.S. Pat. No. 4,487,847 disclose ethylene oligomerization and ethylene dimerization catalyst systems and processes. Efforts to raise the productivity and selectivity of ethylene dimerization and ethylene oligomerization catalysts and processes is ongoing due to the increasing importance of molecules having a molecular weight greater than ethylene.

SUMMARY OF THE INVENTION

It is an object of this invention to provide an improved ethylene oligomerization catalyst system.

It is another object of this invention to provide an improved ethylene oligomerization process.

In accordance with this invention an ethylene oligomerization catalyst system is provided. This catalytic system is produced by the process consisting essentially of: contacting an organonickel compound, an aromatic acid compound, and a phosphine compound.

In accordance with another embodiment of this invention an ethylene oligomerization process is provided. This process consists essentially of: contacting ethylene with the above-mentioned catalytic system.

DETAILED DESCRIPTION OF THE INVENTION

In general, the oligomerization catalyst system of the invention comprises the following components: an organonickel compound, a phosphine compound, and an aromatic acid compound.

The characteristics of the organonickel compound are as follows. The nickel component of the compound should already be in the zero valence state or it should be able to undergo reduction to the zero valence state. The organic component should be an unsaturated group. Suitable examples of organonickel compounds include, but are not limited to, bis(1,5-cyclooctadiene)-nickel, bis(tricyclohexylphosphine)nickel, nickel tetracarbonyl, (cyclododecatriene)nickel, bis(ethylene)(-dicyclohexylphosphine)nickel, tetrakis(triphenylphosphine)nickel, and bis(triphenylphosphine)nickel dicarbonyl. Bis(1,5-cyclooctadiene)nickel is particularly preferred. Additionally, mixtures of two or more organonickel compounds are within the scope of this invention.

The phosphine compound has a general formula $PR_3$, wherein R is independently selected from the group consisting of hydrogen and hydrocarbyl radicals, provided that the hydrocarbyl radical has 1 to about 20 carbon atoms and that any alkenyl substitution be at least 3 carbon atoms removed from the phosphorus atom and at least one R is not hydrogen. Suitable examples of phosphine compounds include, but are not limited to, dicyclohexylphosphine, tricyclohexylphosphine, triethylphosphine, tributylphosphine, diethylphenylphosphine, dicyclohexylphenylphosphine, tribenzylphosphine, ortho-tolyldiphenylphosphine, di(ortho-tolyl)phenylphosphine, triisopropylphosphine, triisobutylphosphine, triterbutylphosphine, phenylphosphine, diphenylphosphine and triphenylphosphine. The most preferred compounds are dicyclohexylphosphine and tricyclohexylphosphine. Additionally, mixtures of two or more phosphines are within the scope of this invention.

The molar ratio of the phosphine compound to nickel is from about 0.01 to about 100. Preferably the molar ratio is from about 0.1 to about 10, and most preferably the molar ratio is 0.5 to 5 due to productivity and selectivity reasons.

The aromatic acid compound has the following formula:

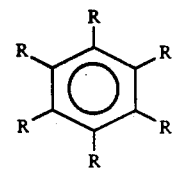

wherein each R is independently selected from the group consisting of hydrogen and hydroxyl groups (—OH) provided that at least one R is not hydrogen. Suitable examples of the aromatic acid compound are phenol, 1,2-dihydroxybenzene, 1,3-dihydroxybenzene, 1,4-dihydroxybenzene, 1,4-dihydroxybenzene, 1,2,3-trihydroxybenzene, 1,2,4-trihydroxybenzene, 1,3,5-trihydroxybenzene, and mixtures of two or more said aromatic compounds.

The molar ratio of aromatic acid compound to nickel is from about 1 to 100,000,000. Preferably, the molar ratio is about 1 to about 1,000,000 and most preferably the molar ratio is 1 to 1,000 due to such factors as productivity and selectivity.

The ethylene oligomerization catalyst system can be produced by contacting an organonickel compound, an aromatic acid compound, and a phosphine compound (generically referred to as the reactants). This contacting can be accomplished in any manner known in the art. For example, the reactants can be contacted in a reactor; this reactor can then be agitated by any manner known in the art; the reactants will thus form an ethylene oligomerization catalyst system.

Ethylene can be oligomerized with the above-described catalyst system. The process parameters that are useful in obtaining optimum production are as follows. The reaction temperature is from about 0° C. to about 200° C., preferably about 20° C. to about 120° C. and most preferably 40° C. to 100° C. The reaction pressure is from about 1 to about 10,000 psig, preferably it is from about 100 to about 8,000 psig and most preferably it is from 200 to 5,000 psig. The reaction time is from about 1 minute to about 100 hours, preferably about 10 minutes to about 1,000 minutes, and most preferably 30 minutes to 300 minutes. These various ranges are preferred due to such factors as productivity and selectivity.

EXAMPLE

This example is provided to further assist a person skilled in the art with understanding this invention. The particular reactants, conditions, and the like, are intended to be generally illustrative of this invention and are not meant to be construed as unduly limiting the reasonable scope of this invention.

All runs described in this Example were carried out in a 300 milliliter stainless steel (316-SS) autoclave engineers stirred tank reactor. The following chemicals were commercially available and used as received: bis(1,5-cyclooctadiene)nickel, hereafter referred to as Ni(COD)$_2$; dicyclohexylphosphine, hereafter referred to as DCHP; and phenol, this solution was present in an 88 weight percent aqueous phenol solution.

Product analysis was performed with an HP5890II gas chromatograph using a capillary DB-1(60m) column. The temperature profile was set for 30° C. initially with a 15° C. per minute increase in the temperature until the temperature of 285° C. was reached. This final temperature was then held for 13 minutes. Detection was accomplished with a flame ionization chamber in the area percent mode. Selectivity to 1-butene and the weight percents of the products were determined by this method. The productivity is defined as the dimerization products produced per gram of nickel per hour. This was determined by totalizer readings on the ethylene flow meter.

The reactor was first purged with nitrogen gas to remove any residual air. This was followed by the addition of the following compounds to the reactor:
1. 50 milliliters of the 88 weight percent aqueous phenol solution;
2. 0.198 grams (1.0 millimoles) of TCHP; and
3. 0.275 grams (1.0 millimoles) of Ni(COD)$_2$.

The reactor was then sealed. After the reactor was sealed, it was purged with ethylene to remove the nitrogen gas. The reactor was then pressurized with ethylene. Each run was conducted at a reaction temperature of 50° C. for a reaction time of 120 minutes. The results are presented in Table E1.

TABLE E1

| Run | Ethylene Pressure[1] | Productivity[2] | Weight Percent[3] C$_4$ | Weight Percent[4] 1-butene/C$_4$ |
|---|---|---|---|---|
| 1 | 900 | 2450 | 93 | 92 |
| 2 | 800 | 2850 | 93 | 77 |
| 3 | 700 | 2720 | 95 | 68 |
| 4 | 600 | 2140 | 94 | 69 |
| 5 | 500 | 1480 | 95 | 65 |
| 6 | 400 | 1200 | 96 | 64 |
| 7 | 300 | 950 | 96 | 62 |

[1]The pressure is in psig.
[2]The productivity is expressed in grams of C$_4$ product produced per gram of nickel used per hour.
[3]The weight percent of C$_4$ was determined by taking the total weight of all C$_4$H$_8$ products and dividing by the total weight of all ethylene oligomerization products.
[4]The weight percent of butene was determined by taking the total weight of 1-butene and dividing by the total weight of all C$_4$H$_8$ products produced.

These results indicate that productivities as high as 2850 g/g hr. can be obtained with the invention. Additionally, high selectivities to the C$_4$ product and high selectivities to the 1-butene product can also be achieved.

That which is claimed is:

1. An ethylene oligomerization catalyst system produced by the process consisting essentially of:
    contacting an organonickel compound, an aromatic acid compound, and a phosphine compound;
    wherein the nickel component of said organonickel compound is in the zero valence state or can undergo reduction to the zero valence state, and the organic component of said organonickel compound is an unsaturated organic group; and
    wherein said aromatic acid compound has the following formula

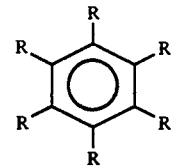

wherein each R is independently selected from the group consisting of hydrogen, and hydroxyl (—OH), provided that, at least one R is not hydrogen; and
    wherein said phosphine compound has the formula PR$_3$, wherein each R is independently selected from the group consisting of hydrogen and hydrocarbyl radicals, provided that said hydrocarbyl radical has 1 to about 20 carbon atoms and that any alkenyl substitution be at least 3 carbon atoms removed from the phosphorous atom and at least one R is not a hydrogen.

2. An ethylene oligomerization catalyst system according to claim 1 wherein said organonickel compound is bis(1,5-cyclooctadiene)nickel, bis(tricyclohexylphosphine)nickel, nickel tetracarbonyl, (cyclododecatriene)nickel, bis(ethylene) (dicyclohexylphosphine)nickel, tetrakis(triphenylphosphine)nickel, bis(triphenylphosphine)nickel dicarbonyl, or mixtures of two or more of said organonickel compounds.

3. An ethylene oligomerization catalyst system according to claim 1 wherein said organonickel compound is bis(1,5-cyclooctadiene)nickel.

4. An ethylene oligomerization catalyst system according to claim 1 wherein said aromatic acid compound is phenol, 1,2-dihydroxybenzene, 1,3-dihydroxybenzene, 1,4-dihydroxybenzene, 1,2,3-trihydroxybenzene, 1,2,4-trihydroxybenzene, 1,3,5-trihydroxybenzene, or mixtures of two or more said aromatic acid compounds.

5. An ethylene oligomerization catalyst system according to claim 1 wherein said aromatic acid compound is phenol.

6. An ethylene oligomerization catalyst system according to claim 1 wherein said phosphine is dicyclohexylphosphine, tricyclohexylphosphine, triethylphosphine, tributylphosphine, diethylphenylphosphine, dicyclohexylphenylphosphine, tribenzylphosphine, ortho-tolyldiphenylphosphine, di(ortho-tolyl)phenylphosphine, triisopropylphosphine, tributylphosphine, tritertbutylphosphine, phenylphosphine, diphenylphosphine, triphenylphosphine, or mixtures of two or more said phosphine compounds.

7. An ethylene oligomerization catalyst system according to claim 1 wherein said phosphine compound is dicyclohexylphosphine.

8. An ethylene oligomerization catalyst system according to claim 1 wherein said phosphine compound is tricyclohexylphosphine.

9. An ethylene oligomerization catalyst system according to claim 1 wherein the molar ratio of phosphine compound to nickel is about 0.1 to about 100.

10. An ethylene oligomerization catalyst system according to claim 1 wherein the molar ratio of phosphine compound to nickel is 0.1 to 10.

11. An ethylene oligomerization catalyst system produced by the process consisting essentially of:
    contacting bis(1,5-cyclooctadiene)nickel, phenol, and dicyclohexylphosphine.

* * * * *